United States Patent
Wilson et al.

(10) Patent No.: US 9,505,792 B2
(45) Date of Patent: Nov. 29, 2016

(54) FORMS OF CIDOFOVIR

(71) Applicant: Johnson Matthey Public Limited Company, London (GB)

(72) Inventors: George Scott Wilson, Edinburgh (GB); Angela Barkley, Westminster, MA (US); Jurjus Jurayj, Acton, MA (US)

(73) Assignee: Johnson Matthey Public Limited Company, London (GB)

(*) Notice: Subject to any disclaimer, the term of this patent is extended or adjusted under 35 U.S.C. 154(b) by 0 days.

(21) Appl. No.: 14/638,595

(22) Filed: Mar. 4, 2015

(65) Prior Publication Data

US 2015/0175640 A1 Jun. 25, 2015

Related U.S. Application Data

(62) Division of application No. 13/441,060, filed on Apr. 6, 2012, now Pat. No. 8,999,958.

(60) Provisional application No. 61/472,843, filed on Apr. 7, 2011.

(51) Int. Cl.
*C07F 9/6512* (2006.01)
*A61K 33/42* (2006.01)

(52) U.S. Cl.
CPC .......... *C07F 9/65121* (2013.01); *A61K 33/42* (2013.01); *C07B 2200/13* (2013.01)

(58) Field of Classification Search
CPC .......................... C07F 9/65121; A61K 33/42
USPC .............................................. 544/243; 514/86
See application file for complete search history.

(56) References Cited

PUBLICATIONS

Cidofovir, Drugs of the Future, 21(10), pp. 1003-1013, 1996.*
Cidofovir: clinical experience and future perspectives, Expert Opinion on Pharmacotherapy, 10(8), pp. 1343-1352 (2009).*
Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*

* cited by examiner

*Primary Examiner* — Deepak Rao
(74) *Attorney, Agent, or Firm* — Shanay M. McCastle

(57) ABSTRACT

Cidofovir is obtained in different forms, including amorphous cidofovir, crystalline anhydrous cidofovir, crystalline cidofovir monohydrate, and crystalline cidofovir dihydrate, including various polymorphs.

3 Claims, 7 Drawing Sheets

FORMS OF CIDOFOVIR

CROSS-REFERENCE TO RELATED APPLICATIONS

This application is a divisional of U.S. patent application Ser. No. 13/441,060, filed Apr. 6, 2012, and claims priority benefit of U.S. Provisional Patent Application No. 61/472,843, filed Apr. 7, 2011, the disclosures of which are incorporated herein by reference in their entireties for all purposes.

FIELD OF THE INVENTION

The present invention generally relates to amorphous and crystalline forms of cidofovir, including polymorphs of crystalline cidofovir, and processes for preparing amorphous and crystalline forms of cidofovir. In particular, the invention is related to novel processes for preparing the amorphous form and the anhydrous, monohydrate, and dihydrate crystalline forms of cidofovir, including various polymorphs.

BACKGROUND OF THE INVENTION

Solids exist in either amorphous or crystalline forms. An anhydrous compound is a compound that does not contain water, especially water of crystallization. A hydrate is any compound containing water in the form of $H_2O$ molecules, usually, but not always, with a definite content of water by weight. The best-known hydrates are crystalline solids that lose their fundamental structures upon removal of the bound water. In the case of crystalline forms, molecules are positioned in three-dimensional lattice sites. When a compound recrystallizes from a solution or slurry, it may recrystallize with different lattice arrangements, and the different crystalline forms are sometimes referred to as "polymorphs." The different crystalline forms or polymorphs of a given substance may differ from each other with respect to one or more physical properties (e.g., mechanical strength, compaction behavior, flow properties, particle size, shape, melting point, degree of hydration or salvation, caking tendency, compactability with excipients), chemical properties (e.g., dissolution rate, solubility), and/or biological properties (e.g., bioavailability, pharmacokinetics). The variation in properties among different crystalline forms often makes one crystalline form more desirable or preferred over other forms.

Cidofovir's chemical formula is $C_8H_{14}N_3O_6P$ and its IUPAC name is ({[(S)-1-(4-amino-2-oxo-1,2-dihydropyrimidin-1-yl)-3-hydroxypropan-2-yl]oxy}methyl)phosphonic acid. Cidofovir has also been described as (S)-(1-(4-amino-2-oxopyrimidin-1(2H)-yl)-3-hydroxypropan-2-yloxy)methylphosphonic acid as well as possibly by other chemical names. Its chemical structure is:

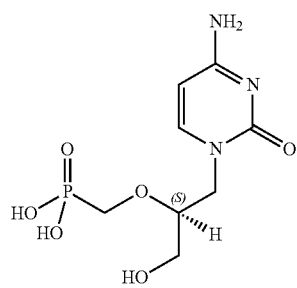

Cidofovir was discovered at the Institute of Organic Chemistry and Biochemistry, Prague, and developed by Gilead Sciences. Today, cidofovir is an injectable antiviral medication for the treatment of cytomegalovirus (CMV) retinitis in patients with AIDS. It suppresses CMV replication by selective inhibition of viral DNA polymerase and therefore prevention of viral replication and transcription. It is an acyclic nucleoside phosphonate, and is therefore independent of phosphorylation by viral enzyme, in contrast to, for instance, acyclovir.

Cidofovir is marketed with the brand name Vistide by Gilead in the United States and by Pfizer in other parts of the world. Vistide® is a sterile, hypertonic aqueous solution for intravenous infusion only. The solution is clear and colorless. It is supplied in clear glass vials, each containing 375 mg of anhydrous cidofovir in 5 mL aqueous solution at a concentration of 75 mg/mL. The formulation is pH-adjusted to 7.4 with sodium hydroxide and/or hydrochloric acid and contains no preservatives. Renal impairment is the major toxicity of Vistide®.

Presently, there are no Orange Book patents listed as having claims which cover Vistide®, although previously U.S. Pat. No. 5,142,051 was listed in the Orange Book for Vistide®. The '051 patent is not directed specifically to cidofovir or its crystalline forms. Instead, it broadly discloses N-phosphonylmethoxyalkyl derivatives of pyrimidine and purine bases.

Because cidofovir has been demonstrated as an effective treatment for patients with AIDS, improved forms of the compound are desired.

SUMMARY OF THE INVENTION

The invention provides crystalline forms of cidofovir and processes for producing crystalline forms of cidofovir. Among the various aspects of the invention is a provision for an amorphous form of cidofovir as well as two anhydrous crystalline forms of cidofovir (Forms I and II).

Another aspect of the invention is a provision for a monohydrate crystalline form of cidofovir (Form III).

Still another aspect of the invention is a provision for two dihydrate crystalline forms of cidofovir (Forms IV and V).

Yet another aspect of the invention is a provision for mixtures of various forms of cidofovir.

Another aspect of the invention provides an amorphous (non-crystalline) form of cidofovir.

A further aspect of the invention encompasses pharmaceutical compositions comprising, or prepared from, amorphous cidofovir and/or crystalline cidofovir Form I and/or crystalline cidofovir Form II and/or crystalline cidofovir Form III and/or crystalline cidofovir Form IV and/or crystalline cidofovir Form V.

An additional aspect of the invention provides processes for preparing amorphous cidofovir and polymorphs of anhydrous, monohydrate and dihydrate forms of cidofovir.

The present invention further provides processes for obtaining substantially pure amorphous and crystalline forms of cidofovir or, if desired, mixtures of different forms of cidofovir.

A pharmaceutical formulation is further provided by the invention, which is prepared by combining at least one form of cidofovir selected from the group consisting of amorphous cidofovir, cidofovir Form I, cidofovir Form II, cidofovir Form III, cidofovir Form IV and cidofovir Form V with at least one pharmaceutically acceptable excipient such as water.

Also provided by the invention is a method of treating a disease, comprising administering to a patient in need of treatment a therapeutically effective amount of at least one form of cidofovir selected from the group consisting of amorphous cidofovir, cidofovir Form I, cidofovir Form II, cidofovir Form III, cidofovir Form IV and cidofovir Form V. The invention also provides a method of treating a disease, comprising administering to a patient in need of treatment a therapeutically effective amount of a pharmaceutical formulation prepared by combining at least one form of cidofovir selected from the group consisting of amorphous cidofovir, cidofovir Form I, cidofovir Form II, cidofovir Form III, cidofovir Form IV and cidofovir Form V with at least one pharmaceutically acceptable excipient such as water.

Other aspects, features and objectives of the invention will be in part apparent and in part described in more detail below.

DETAILED DESCRIPTION OF THE INVENTION

Polymorphism is defined as "the ability of a compound to crystallize in more than one distinct crystal species" and different crystal arrangements of the same chemical composition are termed polymorphs. Polymorphs of the same compound arise due to differences in the internal arrangement of atoms and have different free energies and therefore different physical properties such as solubility, chemical stability, melting point, density, flow properties, bioavailability and so forth.

It has been discovered that cidofovir can be prepared in well-defined and consistently reproducible crystalline forms, as well as mixtures of these forms. More specifically, the inventors have surprisingly found that changing the solvent composition and/or the pH used during product isolation results in different hydrated and polymorphic forms and different impurity profiles being generated. Also, reliable and scalable methods for converting hydrate forms have been developed. Moreover, the cidofovir polymorphs provided by the present invention meet International Conference on Harmonisation (ICH) guidelines and are useful active ingredients in pharmaceutical formulations.

Figure 1:
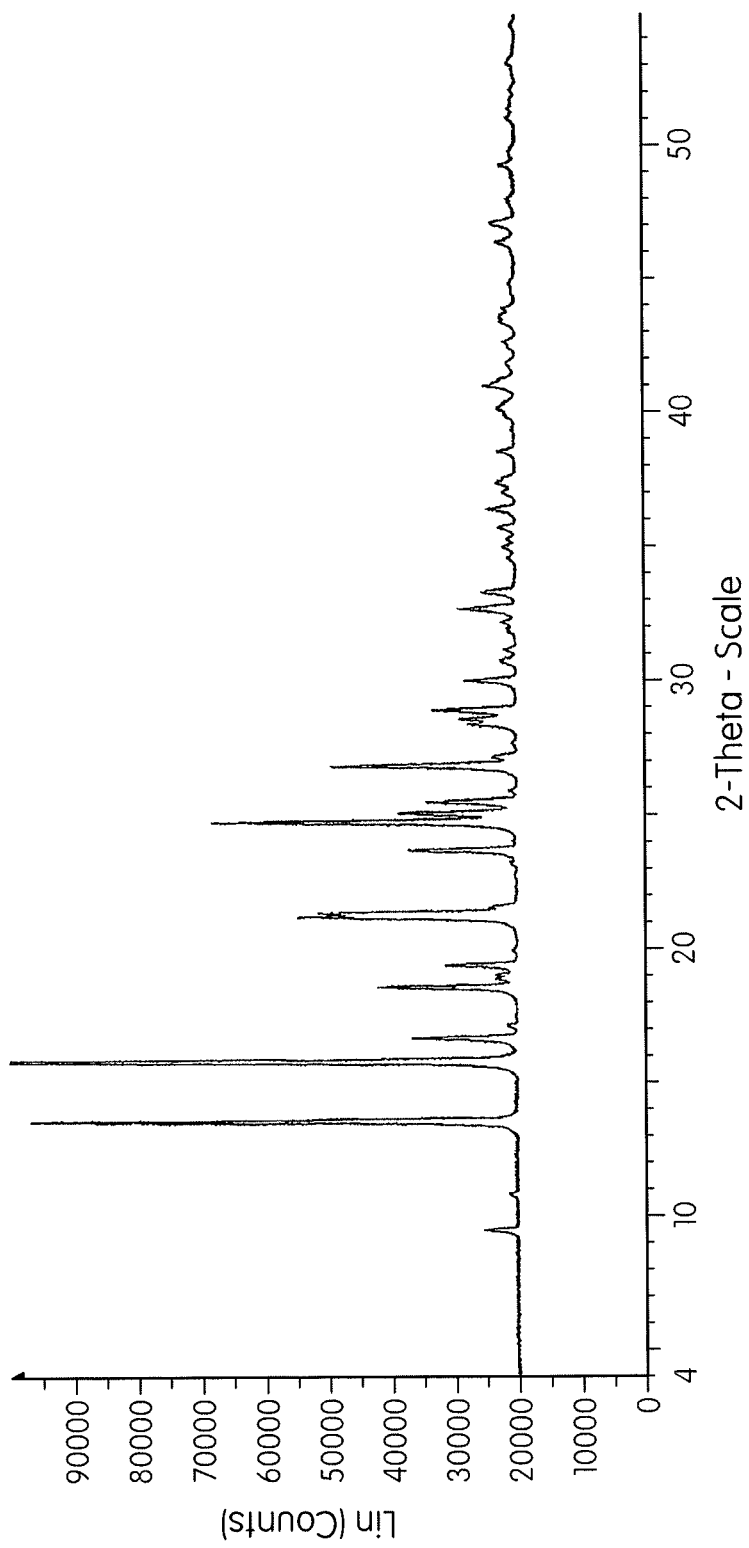
FIG. 1 represents an X-ray powder diffraction (XRPD) pattern of an anhydrous crystalline form of cidofovir (Form I).

One aspect of the invention provides cidofovir Form I. Cidofovir Form I may be characterized by an XRPD pattern substantially in accordance with that shown in FIG. 1, an XRPD 2-theta/intensity/d-value pattern substantially in accordance with that shown in Table A, and/or an XRPD pattern having main peaks expressed as 2-theta at about 15.8, 13.5, 24.9, 21.3, 27.0, 18.6, 25.2, and 23.8 degrees (with "about" herein being understood as modifying each of the stated values). Cidofovir Form I may be in admixture with one or more other forms of cidofovir or may be substantially free of any other physical forms of cidofovir.

Figure 3:
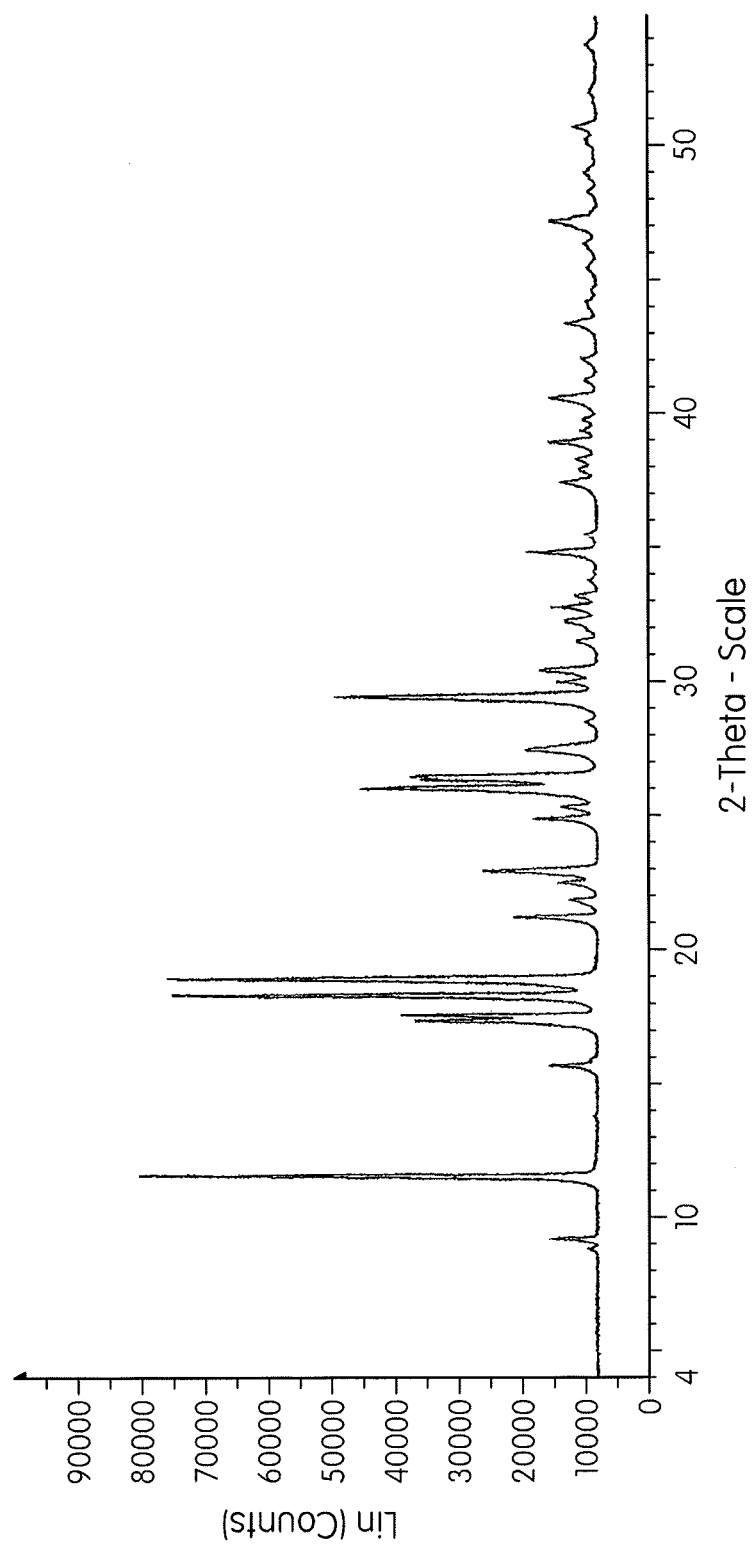
FIG. 3 represents an XRPD pattern of another anhydrous crystalline form of cidofovir (Form II).

Another aspect of the invention provides cidofovir Form II. Cidofovir Form II may be characterized by an XRPD pattern substantially in accordance with that shown in FIG. 3, an XRPD 2-theta/intensity/d-value pattern substantially in accordance with that shown in Table C, and/or an XRPD pattern having main peaks expressed as 2-theta at about 11.5, 19.0, 18.4, 29.7, 26.2, 17.6, 17.4, 26.6, 23.1 and 21.3 degrees. Cidofovir Form II may be in admixture with one or more other forms of cidofovir or may be substantially free of any other physical forms of cidofovir.

Figure 4:
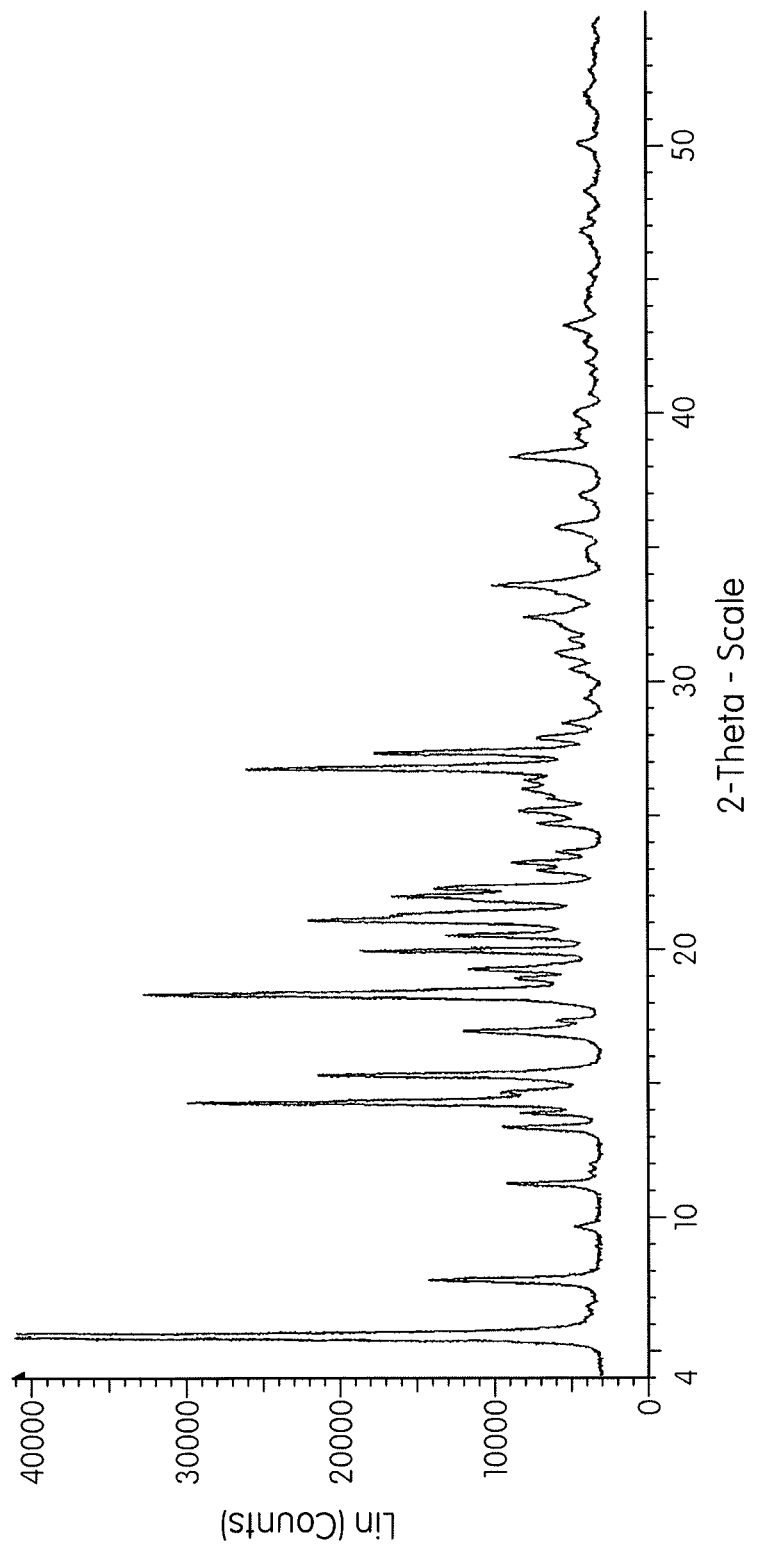
FIG. 4 represents an XRPD pattern of a monohydrate crystalline form of cidofovir (Form III).

In still another aspect of the invention cidofovir Form III is provided. Cidofovir Form III may be characterized by an XRPD pattern substantially in accordance with that shown in FIG. 4, an XRPD 2-theta/intensity/d-value pattern substantially in accordance with that shown in Table D, and/or an XRPD pattern having main peaks expressed as 2-theta at about 5.5, 18.3, 14.2, 26.9, 21.1, 15.2, 19.9, 27.5, 21.3, 22.0, 7.6 and 22.3 degrees. Cidofovir Form III may be in admixture with one or more other forms of cidofovir or may be substantially free of any other physical forms of cidofovir.

Figure 5:
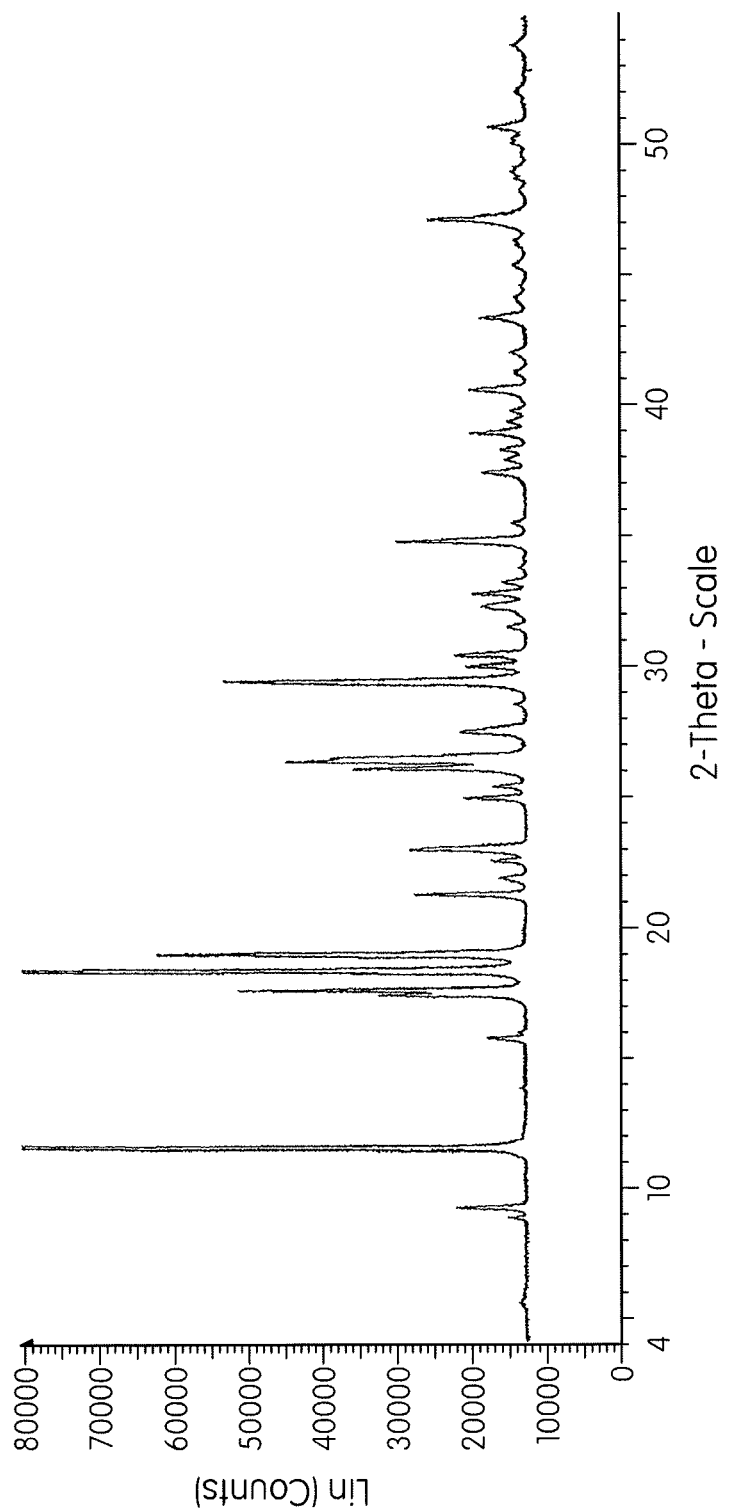
FIG. 5 represents an XRPD pattern of a dihydrate crystalline form of cidofovir (Form IV).

Cidofovir Form IV is provided in yet another aspect of the invention. Cidofovir Form IV may be characterized by an XRPD pattern substantially in accordance with that shown in FIG. 5, an XRPD 2-theta/intensity/d-value pattern substantially in accordance with that shown in Table E, and/or an XRPD pattern having main peaks expressed as 2-theta at about 11.5, 18.4, 19.0, 29.7, 17.6, 26.6, 26.2 and 17.4 degrees. Cidofovir Form IV may be in admixture with one or more other forms of cidofovir or may be substantially free of any other physical forms of cidofovir.

Figure 6:
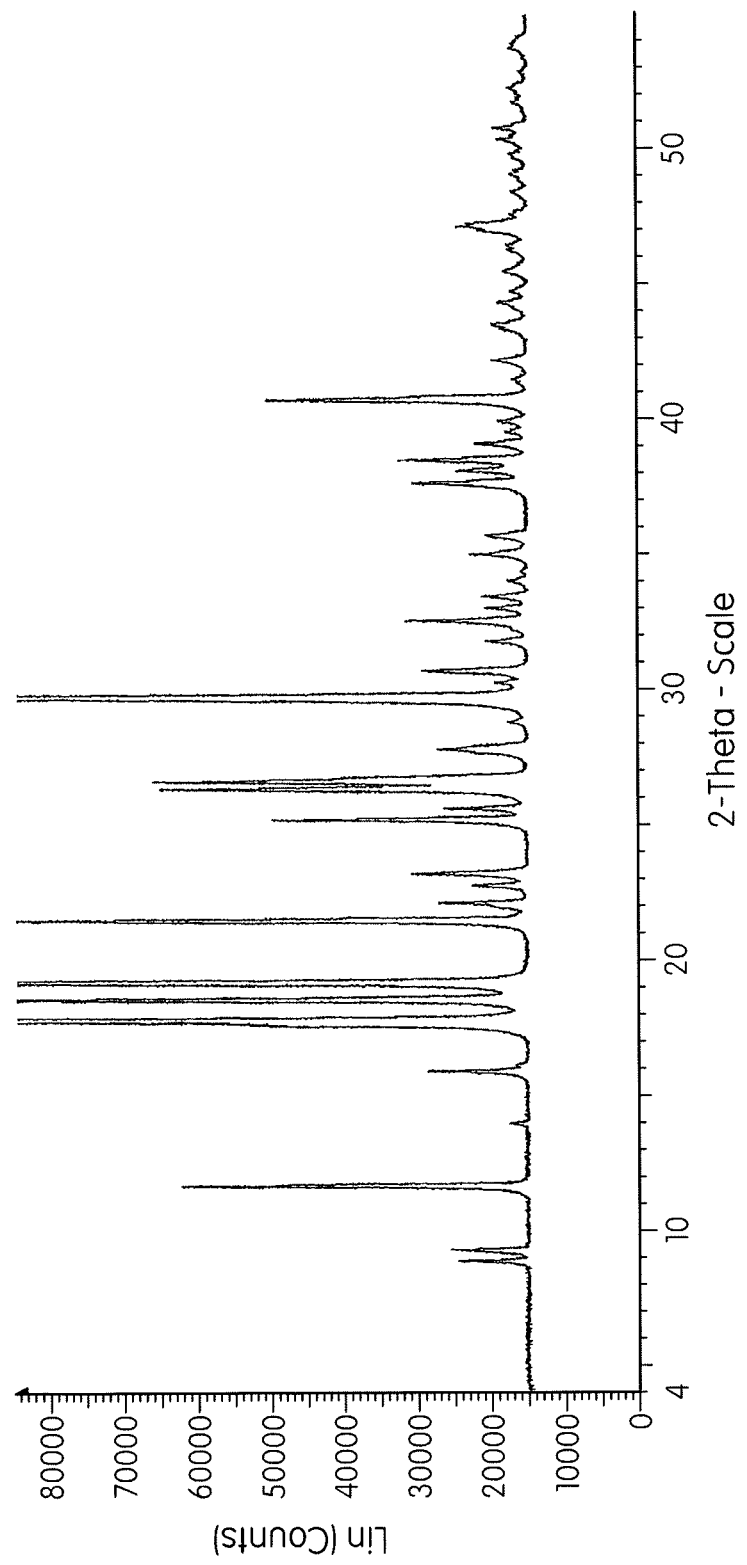
FIG. 6 represents an XRPD pattern of another dihydrate crystalline form of cidofovir (Form V).

A further aspect of the invention provides cidofovir Form V, which may be characterized by an XRPD pattern substantially in accordance with that shown in FIG. 6, an XRPD 2-theta/intensity/d-value pattern substantially in accordance with that shown in Table F, and/or an XRPD pattern having main peaks expressed as 2-theta at about 17.6, 29.7, 19.0, 21.3, 18.4, 26.5, 26.2 and 11.5 degrees. Cidofovir Form V may be in admixture with one or more other forms of cidofovir or may be substantially free of any other physical forms of cidofovir.

A method of preparing anhydrous cidofovir is provided by the present invention, comprising isolating a composition comprised of cidofovir monohydrate at a pH of about 2.5 to about 5.5, combining the composition with water to form a mixture, heating the mixture at a temperature of from about 50° C. to about 80° C., cooling the mixture below about 50° C., and combining the mixture with ethanol to form a slurry comprising anhydrous cidofovir.

An additional aspect of the invention provides amorphous cidofovir, which is non-crystalline and which may be characterized by the substantial absence of any peaks in its XRPD pattern. The amorphous cidofovir may be in admixture with one or more other forms of cidofovir or may be substantially free of any other physical form of cidofovir.

A yet further aspect of the invention provides a method of making cidofovir dihydrate, comprising treating a composition comprised of cidofovir monohydrate isolated at a pH of about 4.5 to about 5.5 with water at a temperature of from about 50° C. to about 80° C. and combining with a volume of ethanol effective to precipitate cidofovir dihydrate. Another method of making cidofovir dihydrate is also provided by the invention, comprising combining a composition comprising cidofovir monohydrate isolated at a pH of about 4.5 to about 5.5 with water to form a mixture, acidifying the mixture, and combining the mixture with ethanol. Still another method of making cidofovir dihydrate provided by the invention comprises slurrying a composition comprising cidofovir monohydrate with aqueous ethanol at a temperature of from about 15° C. to about 35° C.

A method of making cidofovir Form III is further provided by the invention, comprising treating a solution of cidofovir with a base to achieve a pH of about 4.5 to about 5.5 and combining the solution with an amount of ethanol effective to cause precipitation of cidofovir.

Figure 7:
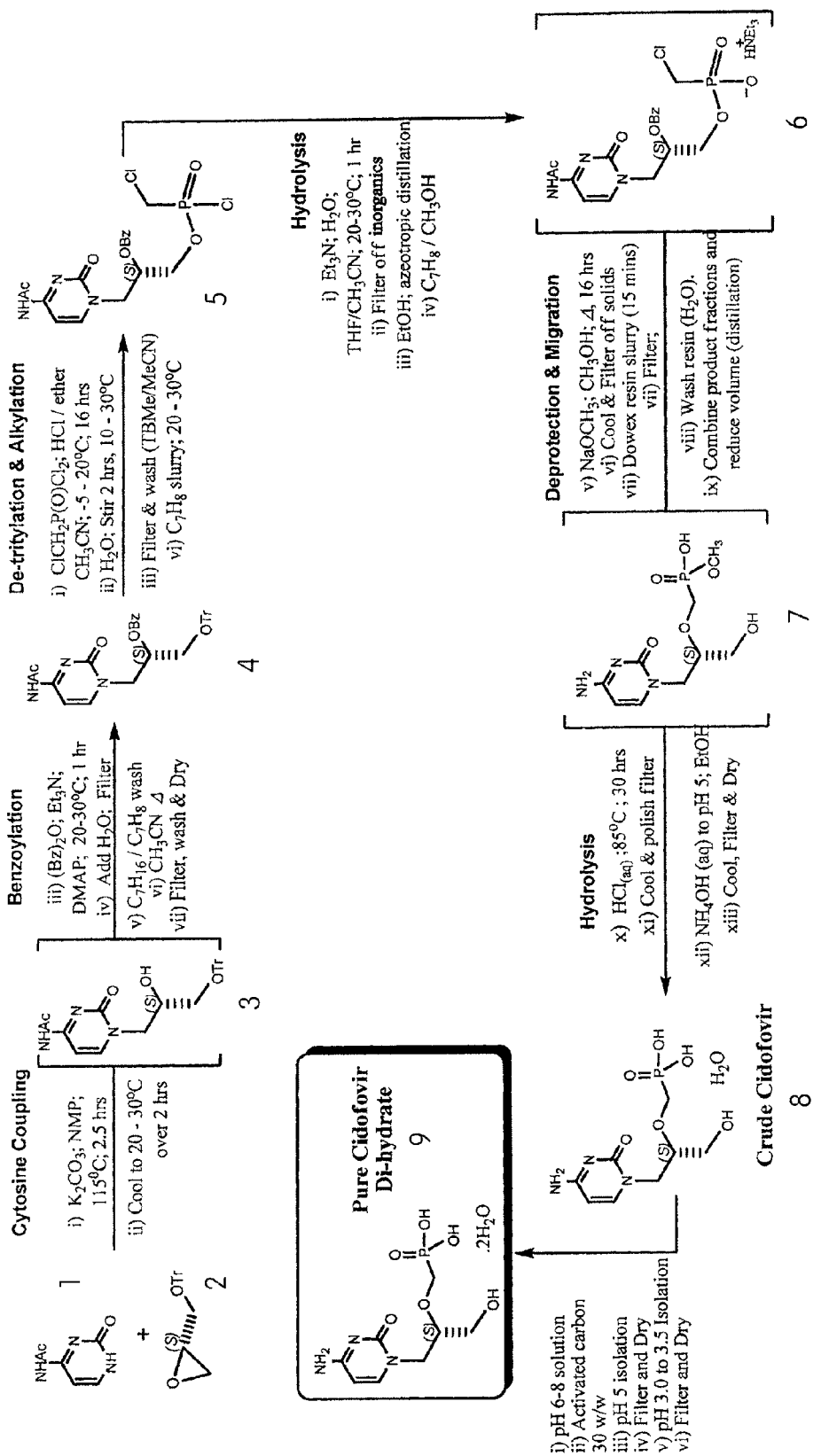
FIG. 7 shows a flow diagram outlining various aspects of the invention, including the synthesis of cidofovir.

FIG. 7 is a flow diagram outlining various aspects of the invention, which are explained in further detail below.

As indicated by FIG. 7, a first step in making cidofovir involves a cytosine coupling reaction in which compound 1 is coupled to compound 2 to provide compound 3. The coupling reaction may be promoted by use of a base. A benzoylation step provides compound 4. De-tritylation and alkylation converts compound 4 to compound 5. In this step, compound 4 is reacted with $ClCH_2P(O)Cl_2$ to replace the trityl group with $—P(O)(Cl)CH_2Cl$.

Compound 5 is hydrolyzed to compound 6 by, for example, stirring in tetrahydrofuran (THF), acetonitrile (ACN), water and $NEt_3$ (triethylamine). It is also preferred that the stirring takes place for a minimum of 1 hour. This reaction mixture is filtered and the solids are washed with THF. If desired, the filtrate is concentrated and washed or chased with solvent to minimize the amount of water in the filtrate. Preferably, the filtrate is chased with the solvent more than once. It is also preferred that the solvent is a toluene/methanol mixture, more preferably a 1:1 toluene/methanol mixture. It is further preferred that the amount of water present in the filtrate is reduced to a Karl Fischer result of less than 1.0%.

In the next step, compound 6 is converted to compound 7, wherein deprotection (removal of the Bz group) and migration of the $—P(O)(Cl)CH_2Cl$ group to the deprotected site take place. For example, the concentrated filtrate material containing compound 6 may be combined with an alcohol, e.g., methanol. In one embodiment, the amount of alcohol added is 3 to 4 volumes based on compound 5. $NaOCH_3$ (e.g., 4.9 eq) is also charged. In one embodiment, this reaction mixture is heated to 30-35° C. and refluxed until the deprotected compound 6 starting material is <1.0% by HPLC. Refluxing may, in one embodiment, be carried out for a minimum of 20 hours.

Next, the solids are filtered and washed with methanol and the combined filtrate is treated with a cation exchange resin to an acidic pH. Preferably, the resin is Dowex® 50WX8 100-200 (H) resin and the pH is 3.0 to 3.5. After filtration and washing of the resin with water, the filtrate (containing compound 7) is concentrated. Preferably, the filtrate is concentrated to 3 mL/g of the calculated initial amount of compound 5. Compound 7 is then hydrolyzed to cidofovir (compound 8). In this step, concentrated hydrochloric acid (8.4 eq) may be charged to the concentrated filtrate and the mixture heated until the compound 7 starting material is less than about 1.0% by HPLC. Preferably, the mixture is heated to a temperature of about 85 to 90° C. for at least 20 hours. This solution is cooled and filtered through a micron filter, preferably a 0.2 micron filter. Ammonium hydroxide, preferably at a concentration of about 30%, is charged to the solution until a pH of about 5.0 is attained. After a constant pH is achieved, ethanol is charged and the solution is stirred. Preferably, 1 volume of ethanol is charged and the solution is stirred for at least 15 minutes. As a precipitate may form during this step, it may be necessary to add more ethanol to the solution/slurry before cooling. After mixing, the solution or mixture is cooled, preferably, to about 5±5° C. and stirred, preferably for at least 12 hours.

At this point, the resultant solid (compound 8, crude cidofovir) can be collected, e.g., by filtration, washed with an alcohol/water mixture, preferably 2:1 $EtOH/H_2O$, and dried under vacuum. Preferably, the solid is dried to a point where there is no weight loss over time (i.e., to a constant weight) at a temperature of about 40° C. The resultant solid is crystalline cidofovir (as a monohydrate).

The above-described method is exemplary. Other methods of synthesizing cidofovir, including methods known in the art, may be utilized.

The relatively crude cidofovir obtained by the foregoing procedure may be further purified and converted to the dihydrate form as follows. The crystalline cidofovir (monohydrate) is slurried in water, preferably to a concentration of about 3 mL/g. The pH is increased, preferably to about pH 6-8, in order to dissolve the cidofovir. It is also preferred that the pH is increased using ammonium hydroxide, most preferably at a concentration of about 28-30%. If desired, activated carbon can be charged to reduce the color of the solution. Preferably, the carbon is added for a period of time until a pale straw colored solution is achieved. More preferably, the carbon is a 12×20 mesh 30% (wt/wt) and is charged and stirred for about 4 to 5 hours. The carbon is filtered through a micron filter, preferably a 0.2 micron filter, and washed with water (1.5 weight/g crude and 1.0 weight/g crude). All solutions are polish filtered. The pH of the combined filtrate and washes is then reduced, preferably to about pH 5 using a concentrated hydrochloric acid (e.g., 3 M) and ethanol (6 volume) mixture. This results in a slurry which is then cooled, preferably to about 5±5° C., and stirred, preferably for at least 12 hours. The solid portion of the slurry is isolated by filtration, washed with an alcohol/water mixture, preferably 2:1 $EtOH/H_2O$, and dried. Preferably, the filtered solid is dried to achieve a constant weight under vacuum at a temperature of about 40° C.

The isolated solid is then combined with water, preferably to a concentration of 5 mL/g. Concentrated HCl, preferably 3 M HCl, is added to obtain a pH of about pH 3.0-3.5. Alcohol, preferably 3 volumes of ethanol, is charged and the mixture is cooled and stirred. Preferably, the temperature of the mixture is reduced to about 5±5° C. after which stirring occurs for at least 12 hours. The precipitated solid is then isolated by filtration and washed, preferably with 2:1 $EtOH/H_2O$. Drying to constant weight under vacuum at 40° C. results in cidofovir dihydrate (compound 9).

Four separate HPLC methods have been identified for monitoring the process, intermediates and final product, including one to confirm the chiral purity of the final product. The methods have been optimized and shown to be scientifically robust. Impurity marker qualification was conducted resulting in more than 20 potential impurities in the process although a number of the impurities are only observed in trace levels.

Methods for determining residual levels of genotoxic impurities and reagents have been developed although so far it is believed that such a method is only required for residual DMAP reagent, which is used during the first stage of the process and is removed during later processing stages.

An appropriate gas chromatography (GC) method for determining residual solvent levels in the final product was developed. Stability indicating methods were also developed and conducted on the final products.

A full monograph for the final crystalline cidofovir dihydrate product (compound 9) has been completed and it was confirmed that, with an OEL of 0.6 μgm$^{-3}$, the product remains within category band 5 (safebridge category 3). This assessment also suggests that processing intermediates up to and including compound 6 can be handled with a lower level of containment than compounds 7 to 9.

The inventors have also discovered the following features of their invention as a result of conducting numerous experiments:

Preparation Procedures:

1. Isolations at pH 3.5-5 (see, e.g., FIG. 7) yield various hydrated forms of cidofovir, including dihydrate, depending on the solvent conditions used.

2. Isolations at pH 3.5 result in high levels of a residual impurity (uracil impurity) and require multiple treatments to reduce levels within specification. Note: this impurity can be reduced by adjusting the pH to 5 using ammonium hydroxide and precipitating the material with ethanol (3 vol).

3. Isolations at pH 5 result in high quality product (within ICH guidelines) in various hydrated forms depending on the solvent conditions used. Treatment of the crude cidofovir isolated at pH 5 with various treatments gives high purity HPLC material.

Interconversions:

4. Cidofovir dihydrate may be prepared by a process comprising treating a composition comprised of cidofovir monohydrate isolated at a pH of about 4.5 to about 5.5 with water at a temperature of from about 50° C. to about 80° C. and combining with a volume of ethanol effective to precipitate cidofovir dihydrate. For example, treatment of the crude material (monohydrate or mixtures) isolated at pH 5 with 6.6 mL water/g at 65° C. followed by precipitation with 1 vol ethanol gives pure cidofovir dihydrate. In another suitable process for obtaining cidofovir dihydrate, a composition comprised of cidofovir monohydrate isolated at a pH of about 4.5 to about 5.5 is combined with water to form a mixture, the mixture is acidified (e.g., to a pH of about 2.5 to about 4 or about 3 to about 3.5) using a suitable acid (e.g., HCl) and combined with ethanol. The mixture may be cooled below room temperature (e.g., to about 0° C. to about 10° C.) and stirred for a period of time (e.g., about 6 to about 24 hours, preferably at least about 12 hours) to provide pure cidofovir dihydrate. The cidofovir dihydrate may be collected by a suitable method (e.g., filtration), washed and/or dried.

5. Isolation of cidofovir at a pH of about 2.5 to about 5.5 (e.g., 3, 3.5 or 5) followed by different precipitation protocols can give rise to anhydrous forms of cidofovir. The crude cidofovir material (containing cidofovir monohydrate) does not dissolve in water at 65° C.-30 mL water was used and the mixture was cooled to 40° C. and 1 vol EtOH added to give a material with 0.2% KF (0.2% water as measured by Karl Fischer). The invention thus provides a method of making anhydrous cidofovir (Form I or Form II) comprising isolating a composition comprised of cidofovir monohydrate at a pH of about 2.5 to about 5.5, combining the composition with water to form a mixture, heating the mixture at a temperature of from about 50° C. to about 80° C., cooling the mixture below about 50° C., and combining the mixture with ethanol to form a slurry comprising anhydrous cidofovir. The use of relatively larger amounts of ethanol favors the formation of the Form I polymorph. For example, if the amount of ethanol is approximately 1 volume per volume of water, the Form II polymorph may be obtained, whereas if the amount of ethanol is approximately 7 volumes per volume of water, the Form I polymorph may be obtained. The anhydrous cidofovir may be isolated by a suitable separation means (e.g., filtration), washed and/or dried.

6. Conversion from a form with a Karl Fischer value of about 7% (corresponding to a monohydrate) to a form with a Karl Fischer value of about 11.3% (corresponding to a dihydrate) is possible by slurrying the crude material at about room temperature with aqueous ethanol (e.g., 1:1 EtOH/H$_2$O). The invention thus provides a method of making cidofovir dihydrate, comprising slurrying a composition comprised of cidofovir monohydrate with aqueous ethanol at a temperature of from about 15° C. to about 35° C.

Cidofovir monohydrate Form III may be obtained by a method comprising treating a solution of cidofovir with a base to achieve a pH of about 4.5 to about 5.5 and combining the solution with an amount of ethanol effective to cause precipitation of cidofovir. The initial cidofovir solution may, for example, be an acidified solution obtained as a result of hydrolyzing compound 7 in FIG. 7. Such solution, following the hydrolysis step (which typically involves treatment of compound 7 with a strong acid such as HCl and heating to an elevated temperature, e.g., about 75° C. to about 100° C., for a period of time effective to achieve hydrolysis of the phosphate ester group), may be filtered to remove any residual solid impurities prior to treatment with a base (e.g., ammonium hydroxide). After combining with ethanol (which may be added in portions), the resulting mixture may be cooled (e.g., to a temperature of from about 0° C. to about 10° C. and stirred for a period of time (e.g., at least about 12 hours) before isolating the precipitated cidofovir monohydrate Form III by a suitable means such as filtration. The collected precipitate may be washed (e.g., with aqueous ethanol) and then dried to constant weight (e.g., at a temperature of about 30° C. to about 50° C. under vacuum).

Amorphous cidofovir may be obtained by freeze-drying (lyophilizing) a solution of cidofovir as well as by precipitating cidovir from an aqueous solution. For example, an aqueous solution of cidofovir may be prepared (e.g., by combining solid cidofovir and water and adding ammonium hydroxide until dissolution is achieved). An acid such as HCl may then be added to lower the pH to about 3.5 to about 4.5 (e.g., a pH of about 4) and ethanol thereafter added to obtain precipitated solids. The mixture may be cooled below room temperature (e.g., −20 to −15° C.) for a period of time (e.g., 1 to 24 hours) and the solids then isolated (by filtration, for example), washed (with aqueous ethanol, for example), and dried (e.g., under vacuum at 20 to 40° C.) to provide amorphous cidofovir.

Mixtures of the above-described different cidofovir forms may be obtained by varying the isolation and recrystallization as well as by separately preparing different forms as pure substances and combining such pure substances together.

A pharmaceutical formulation may be prepared by combining or formulating at least one form of cidofovir selected from the group consisting of amorphous cidofovir, cidofovir Form I, cidofovir Form II, cidofovir Form III, cidofovir Form IV and cidofovir Form V with at least one pharmaceutically acceptable excipient. Suitable excipients include any of the known or conventional ingredients or components useful to include in pharmaceutical formulations in addition to the active pharmaceutical ingredient(s), including, for example, carriers, diluents, solvents (e.g., water), preservatives, stabilizers, pH adjusting agents, wetting agents and the like. The pharmaceutical formulation can take the form of powders, suspensions, solutions, sprays, emulsions, pastes, ointments and the like and can be used, for example, for parenteral administration (intravenous, intradermal, intramuscular, intrethecal, etc.) as well as for oral, rectal, intravaginal or intranasal administration or topical administration. According to the requirements and application form, these formulations can contain various concentrations of one or more forms of cidofovir in accordance with the invention, from about 0.01 up to 100% by weight, for example. Pharmaceutical formulations in accordance with the invention may be utilized to treat any of the conditions or diseases where cidofovir is known to have efficacy, including for example in the treatment of cytomegalovirus (CMV) retinitis in patients with AIDS.

In one embodiment of the invention, a quantity of one or more forms of cidofovir in accordance with the invention is dissolved in water (e.g., water suitable for injection) to provide a solution, with the pH of the solution being adjusted to approximately neutral (e.g., 7.4) using a base (e.g., sodium hydroxide) or acid (e.g., HCl). In one embodiment, no preservatives are present in the solution. The concentration of cidofovir may be adjusted as desired; for example, the cidofovir concentration may be about 75 mg/mL (calculated as anhydrous cidofovir). Such a solution may be supplied in clear glass vials, each containing 375 mg of anhydrous cidofovir in 5 mL aqueous solution. The solution may be utilized as an injectable antiviral medication for the treatment of cytomegalovirus (CMV) retinitis in patients with AIDS.

The invention will be illustrated in more detail with reference to the following embodiments and examples, but it should be understood that the present invention is not deemed to be limited thereto.

The different crystalline forms of cidofovir described herein are characterized, for example, by reference to the 2-theta (2-θ) values of their main peaks in their XRPD (X ray powder diffraction) patterns. In various embodiments, each such value is considered to include the range of ±0.4, ±0.3, ±0.2 or ±0.1 from the stated value.

EXAMPLES

Example 1

Amorphous Form of Cidofovir

An amorphous form of cidofovir may be obtained by freeze-drying (lyophilizing) a solution of cidofovir.

Example 2

Anhydrous Form of Cidofovir (Form I)

Crude cidofovir (1.72 g) was isolated at pH 3 and heated to 65° C. in water (30 mL) for 2 hours. The mixture was then cooled to 30° C. after which ethanol (one volume, 30 mL) was charged. A slurry formed and was stirred overnight. The slurry was filtered to collect the solid and then the solid was washed with an ethanol:water (2:1) mixture before drying the crystalline solid. The crystalline solid was determined to be anhydrous containing only about 0.3% by weight water (by Karl Fischer). The crystalline solid (Form I) was analyzed by XRPD which provided the results in FIG. 1 and Table A. Accordingly, Form I is characterized by its XRPD pattern having main peaks expressed as 2-theta at about 15.8, 13.5, 24.9, 21.3, 27.0, 18.6, 25.2, and 23.8 degrees. The cidofovir Form I thus made is therefore substantially free of any other physical forms of cidofovir.

Example 3

Confirmation of Anhydrous Form I of Cidofovir

Figure 2:
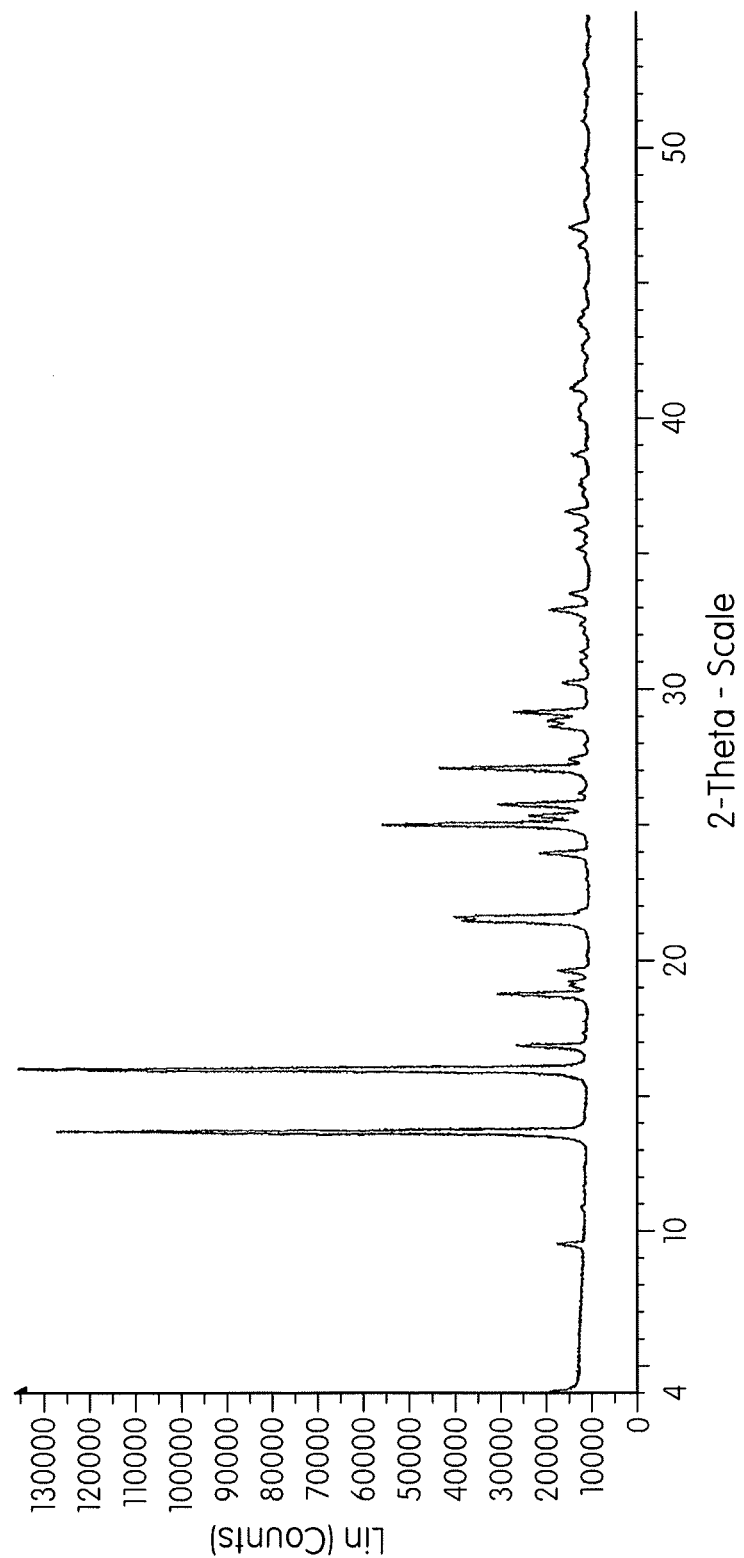
FIG. 2 represents an X-ray powder diffraction (XRPD) pattern of another sample of cidofovir Form I.

Crude cidofovir (1.84 g) was isolated at pH 5 and heated to 65° C. in water (5 mL). The slurry was then cooled to 40° C. after which ethanol (one volume, 6.6 mL) was charged followed by the addition of ethanol (6 volumes). The slurry was stirred overnight. The slurry was filtered to collect the solid and then the solid was washed with an ethanol:water (2:1) mixture before drying the crystalline solid. The crystalline solid was again determined to be anhydrous containing only about 0.3% by weight water (by Karl Fischer). The crystalline solid was analyzed by XRPD and, as shown in FIG. 2 and Table B, is confirmed to be Form I. In this example, the XRPD pattern of the crystalline solid displayed main peaks expressed as 2-theta at about 15.8, 13.5, 24.9, 27.0, 21.4, 18.6, 25.6 and 29.1 degrees.

Example 4

Another Anhydrous Form of Cidofovir (Form II)

The procedure set forth in Example 3 was repeated except that there was no addition of 6 volumes of ethanol. The resultant crystalline solid was determined to be a different anhydrous crystalline form (Form II) from the anhydrous form (Form I) obtained in Examples 2 and 3. The crystalline solid was analyzed by XRPD, which provided the results shown in FIG. 3 and Table C. The XRPD pattern of the crystalline solid displayed main peaks expressed as 2-theta at about 11.5, 19.0, 18.4, 29.7, 26.2, 17.6, 17.4, 26.6, 23.1 and 21.3 degrees.

Example 5

Monohydrate Form of Cidofovir (Form III)

Compound 5 (FIG. 6) is hydrolyzed to compound 6 by stirring in tetrahydrofuran (THF) (8.5 vol), acetonitrile (ACN) (0.5 vol), $H_2O$ (2.0 eq.) and $NEt_3$ (triethylamine) (2.0 eq) for a minimum of 1 hour. This reaction mixture is filtered and the solids washed with THF. The filtrate is concentrated and chased with 1:1 toluene/methanol (2×) to obtain a Karl Fischer value of <1.0%. The concentrated material is taken up in methanol (3 to 4 volumes based on the amount of compound 5), warmed to 30-35° C. and $NaOCH_3$/MeOH (4.9 eq) is charged. This reaction mixture is heated to reflux for a minimum of 20 hours until the amount of deprotected compound 6 starting material is <1.0% by HPLC. The solids are filtered and washed with methanol. The combined filtrate is treated with Dowex® 50WX8 100-200 (H) resin to pH 3.0 to 3.5. After filtration and washing of the resin with water, the filtrate is concentrated to a volume of 3 mL/g of the initial amount of compound 5. Concentrated HCl (8.4 eq) is charged and the mixture heated to 85 to 90° C. for a minimum of 20 hours until the amount of compound 7 starting material is <1.0% by HPLC. This solution is cooled, and filtered through a 0.2 micron filter. Ammonium hydroxide (28-30%) is charged to the solution to pH 5.0. After constant pH is attained, ethanol (1 volume) is charged and stirred for a minimum of 15 minutes. Precipitation usually occurs. Additional ethanol (2 volumes) is charged and the mixture cooled to 5±5° C. and stirred for a minimum of 12 hours. The solid is collected by filtration, washed with 2:1 $EtOH/H_2O$ and dried to constant weight under vacuum at 40° C. to give cidofovir (as a monohydrate). The crystalline solid was determined to be a monohydrate containing about 7% by weight water (by Karl Fischer). The crystalline solid (Form III) was analyzed by XRPD which provided the results in FIG. 4 and Table D. Accordingly, Form III is characterized by an XRPD pattern having main peaks expressed as 2-theta at about 5.5, 18.3, 14.2, 26.9, 21.1, 15.2, 19.9, 27.5, 21.3, 22.0, 7.6 and 22.3 degrees. The cidofovir Form III is substantially free of any other physical forms of cidofovir.

Example 6

Dihydrate Forms of Cidofovir (Forms IV and V)

The procedure set forth above in Example 5 was used to make the monohydrate form of cidofovir. The solid thus obtained is slurried in water (3 mL/g). The pH is adjusted to pH 6-8 for dissolution using ammonium hydroxide (28-30%). Activated carbon 12×20 mesh 30% weight/weight is charged and stirred for 4 to 5 hours and the color of the solution monitored (pale straw colored solution is expected). After the required stir time, the carbon is filtered off through a 0.2 micron filter. The carbon is washed with water (1.5 weight/g crude and 1.0 weight/g crude). All solutions are polish filtered. The combined filtrate and washes are adjusted to pH 5 with 3M HCl and ethanol (6 volumes) is charged. This slurry is cooled to 5±5° C. and stirred for a minimum of 12 h. The solid is isolated by filtration, washed with 2:1 EtOH/H$_2$O and dried to constant weight under vacuum at 40° C. to give the pH 5 solid. This isolated solid is taken up in water (5 mL/g of the pH 5 solid) and 3M HCl is carefully added to a constant pH of pH 3.0 to 3.5. Ethanol (3 volumes) is charged. This mixture is cooled to 5±5° C. and stirred for a minimum of 12 hours. The solid is isolated by filtration and washed with 2:1 EtOH/H$_2$O, then dried to constant weight under vacuum at 40° C. to provide cidofovir dihydrate.

The crystalline form of cidofovir dihydrate has been found to vary somewhat depending upon the conditions used to prepare it. At present, it is believed that cidofovir dihydrate has been isolated in two different crystalline forms, referred to herein as Form IV and Form V, which have somewhat similar (yet different) X-ray powder diffraction patterns. One representative sample of cidofovir dihydrate Form IV (Sample 6-2 in the table below) was analyzed by XRPD to provide the results shown in FIG. 5 and Table E. This sample was characterized by an XRPD pattern having main peaks expressed as 2-theta at about 11.5, 18.4, 19.0, 29.7, 17.6, 26.6, 26.2 and 17.4 degrees. A representative sample of cidofovir dihydrate Form V (Sample 6-1 in the table below) was analyzed by XRPD to provide the results shown in FIG. 6 and Table F. This sample was characterized by an XRPD pattern having main peaks expressed as 2-theta at about 17.6, 29.7, 19.0, 21.3, 18.4, 26.5, 26.2 and 11.5 degrees.

The following table provides a summary of certain experiments conducted by the inventors for the purpose of identifying the conditions which produce either the Form IV or Form V of cidofovir dihydrate.

| Sample No. | Treatment of Cidofovir solid | Isolation of solid | KF | Form |
|---|---|---|---|---|
| 6-1 | 1.02 g/6.6 mL H$_2$O at 65° C. | 1 vol EtOH at 40° C. | 11.6% | V |
| 6-2 | Dried in oven 35° C. | pH 3.5 | 12.1% | IV |
| 6-3 | Dried at room temperature | pH 3.5 | 11.6% | IV |
| 6-4 | Heated in 11.5 mL water (5 mL/g crude) at 65° C. | 1 vol EtOH at 40° C. then 6 vol EtOH at room temperature | 11.5% | IV |

Example 7

Amorphous Cidofovir

Intermediate 5 (FIG. 7; 0.5 g, 0.054 mol) was heated with a solution of sodium methoxide in methanol (0.5 M, 15 mL, 7.5 mmol) at 72° C. for 14.5 h then at 90° C. for 5.5 h. The reaction mixture was quenched with water (10 mL) and filtered through a bed of ion exchange resin Dowex® 50WX8 100-200 (H). The filtrate was cycled through the ion exchange bed (2 times) then washed successively with 1:1 methanol:water (40 mL), methanol (40 mL) and 4% triethylamine:methanol (50 mL). This ion-exchange bed was further washed with 48:48:4 methanol:water:triethylamine (100 mL) until no UV absorbance was detected in the filtrate. This reaction produced intermediate 7 (FIG. 7) together with cyclic cidofovir impurity. This mixture was then dissolved in 6 N HCl and heated to 65° C. After cooling the reaction mixture to room temperature, ethyl acetate was charged and stirred and the aqueous layer separated. The aqueous was stirred with ethanol (50 mL). The precipitated material was filtered and the solid was washed with ethanol. The ethanol filtrate was concentrated. The concentrated material was taken up in acetonitrile and stirred with trimethylsilyl bromide (19 mL) at room temperature for 18 h. The reaction mixture was filtered and the filtrate concentrated. The residue was taken up in toluene (30 mL) and ammonium hydroxide (28%, 50 mL) was charged and stirred at room temperature. The organic phase was separated and the aqueous phase was concentrated to dryness. Water (20 mL) and ethanol (15 mL) were added to the residue. The mixture pH was 6 and was adjusted to pH 3 with concentrated HCl (2 mL) then adjusted to pH 4 to 4.5 with 28% NH$_4$OH. After stirring for 0.5 h, the mixture was cooled, filtered and the solids washed with 2:1 EtOH:H$_2$O and dried under vacuum for 18 h. The isolated solid was taken up in water (10 mL) and 28% NH$_4$OH added to give a solution. Concentrated HCl was added to the solution until pH 4 was reached. Ethanol (13 mL) was charged and the mixture stirred at −17° C. for 18 h, filtered and the solids washed with 2:1 EtOH:water (2×8 mL), dried under vacuum at 35° C. The cidofovir isolated in this manner was determined to be in the amorphous form by XRPD.

TABLE A

| Intensity % % | Angle 2-Theta ° | Intensity Count | d value Angstrom |
|---|---|---|---|
| 100.0 | 15.828 | 99902 | 5.59455 |
| 78.8 | 13.525 | 78759 | 6.54140 |
| 49.3 | 24.870 | 49266 | 3.57725 |
| 32.5 | 21.330 | 32513 | 4.16222 |
| 30.6 | 26.982 | 30556 | 3.30183 |
| 23.0 | 18.599 | 22984 | 4.76673 |

TABLE A-continued

| Intensity % % | Angle 2-Theta ° | Intensity Count | d value Angstrom |
|---|---|---|---|
| 20.0 | 25.191 | 19940 | 3.53236 |
| 18.5 | 23.790 | 18454 | 3.73709 |
| 18.2 | 16.677 | 18193 | 5.31174 |
| 15.7 | 25.611 | 15698 | 3.47536 |
| 14.6 | 29.064 | 14563 | 3.06992 |
| 12.5 | 19.428 | 12491 | 4.56534 |
| 10.4 | 28.733 | 10407 | 3.10448 |
| 10.3 | 32.891 | 10300 | 2.72089 |
| 9.5 | 30.183 | 9484 | 2.95857 |
| 9.0 | 28.539 | 9022 | 3.12520 |
| 8.4 | 9.388 | 8401 | 9.41283 |
| 6.5 | 33.504 | 6447 | 2.67251 |
| 6.2 | 41.178 | 6241 | 2.19047 |
| 5.6 | 36.573 | 5644 | 2.45499 |
| 5.2 | 27.311 | 5193 | 3.26279 |
| 4.8 | 47.197 | 4784 | 1.92419 |
| 4.2 | 37.555 | 4173 | 2.39304 |
| 4.0 | 40.335 | 4015 | 2.23428 |
| 4.0 | 10.751 | 4028 | 8.22279 |
| 3.9 | 38.716 | 3924 | 2.32388 |
| 3.8 | 18.974 | 3825 | 4.67349 |
| 3.8 | 46.477 | 3844 | 1.95232 |
| 3.8 | 41.388 | 3779 | 2.17981 |
| 3.8 | 35.895 | 3825 | 2.49982 |
| 3.6 | 30.928 | 3571 | 2.88901 |
| 3.4 | 49.346 | 3408 | 1.84532 |
| 3.4 | 32.374 | 3414 | 2.76314 |
| 3.2 | 43.575 | 3207 | 2.07536 |
| 3.2 | 35.178 | 3201 | 2.54905 |
| 3.2 | 40.542 | 3179 | 2.22333 |
| 3.1 | 17.155 | 3058 | 5.16476 |
| 3.1 | 44.016 | 3113 | 2.05560 |
| 3.1 | 37.201 | 3099 | 2.41499 |
| 3.1 | 37.748 | 3067 | 2.38124 |
| 3.0 | 31.354 | 3028 | 2.85070 |
| 2.9 | 40.090 | 2898 | 2.24738 |
| 2.9 | 12.206 | 2918 | 7.24542 |
| 2.8 | 42.792 | 2838 | 2.11151 |
| 2.7 | 42.023 | 2718 | 2.14837 |
| 2.7 | 26.043 | 2683 | 3.41871 |
| 2.6 | 14.254 | 2571 | 6.20867 |
| 2.5 | 32.093 | 2459 | 2.78674 |
| 2.5 | 35.501 | 2529 | 2.52663 |
| 2.4 | 51.096 | 2408 | 1.78613 |
| 2.4 | 23.313 | 2425 | 3.81253 |
| 2.4 | 34.796 | 2424 | 2.57621 |
| 2.3 | 48.103 | 2260 | 1.89005 |
| 2.2 | 53.162 | 2199 | 1.72150 |
| 2.1 | 51.443 | 2128 | 1.77489 |
| 2.1 | 27.848 | 2140 | 3.20110 |
| 2.1 | 44.919 | 2118 | 2.01632 |
| 2.0 | 20.005 | 2030 | 4.43490 |
| 2.0 | 49.833 | 2028 | 1.82840 |
| 1.9 | 52.133 | 1908 | 1.75300 |
| 1.9 | 22.849 | 1879 | 3.88898 |
| 1.9 | 39.555 | 1890 | 2.27653 |
| 1.8 | 51.738 | 1821 | 1.76547 |
| 1.7 | 44.625 | 1703 | 2.02893 |
| 1.6 | 54.507 | 1606 | 1.68214 |
| 1.5 | 48.964 | 1470 | 1.85878 |
| 1.5 | 46.052 | 1538 | 1.96932 |
| 1.5 | 52.821 | 1487 | 1.73178 |
| 1.4 | 53.687 | 1351 | 1.70589 |
| 1.3 | 45.403 | 1326 | 1.99597 |
| 1.2 | 50.441 | 1166 | 1.80779 |

TABLE B

| Intensity % % | Angle 2-Theta ° | Intensity Count | d value Angstrom |
|---|---|---|---|
| 100.0 | 15.832 | 135966 | 5.59306 |
| 87.3 | 13.534 | 118705 | 6.53738 |
| 34.7 | 24.863 | 47148 | 3.57832 |
| 25.3 | 26.975 | 34460 | 3.30274 |
| 22.4 | 21.375 | 30457 | 4.15364 |

TABLE B-continued

| Intensity % % | Angle 2-Theta ° | Intensity Count | d value Angstrom |
|---|---|---|---|
| 16.0 | 18.596 | 21821 | 4.76764 |
| 15.8 | 25.609 | 21521 | 3.47570 |
| 13.3 | 29.070 | 18131 | 3.06924 |
| 12.7 | 16.675 | 17276 | 5.31230 |
| 10.7 | 25.195 | 14496 | 3.53188 |
| 8.9 | 23.789 | 12155 | 3.73730 |
| 7.5 | 28.741 | 10251 | 3.10368 |
| 7.2 | 28.544 | 9785 | 3.12464 |
| 7.1 | 32.900 | 9672 | 2.72019 |
| 6.3 | 9.378 | 8549 | 9.42343 |
| 5.9 | 19.445 | 8037 | 4.56143 |
| 5.1 | 30.196 | 6964 | 2.95734 |
| 4.7 | 36.571 | 6353 | 2.45514 |
| 4.2 | 19.025 | 5776 | 4.66114 |
| 4.2 | 27.319 | 5693 | 3.26190 |
| 3.9 | 47.183 | 5364 | 1.92472 |
| 3.9 | 41.184 | 5238 | 2.19015 |
| 3.9 | 33.506 | 5367 | 2.67240 |
| 3.5 | 38.724 | 4773 | 2.32345 |
| 3.1 | 35.902 | 4178 | 2.49935 |
| 2.8 | 41.369 | 3744 | 2.18080 |
| 2.8 | 35.186 | 3765 | 2.54854 |
| 2.6 | 26.052 | 3510 | 3.41759 |
| 2.6 | 43.735 | 3541 | 2.06811 |
| 2.5 | 40.099 | 3347 | 2.24688 |
| 2.5 | 40.388 | 3352 | 2.23144 |
| 2.4 | 30.973 | 3264 | 2.88487 |
| 2.4 | 46.494 | 3266 | 1.95162 |
| 2.3 | 31.349 | 3084 | 2.85113 |
| 2.3 | 32.381 | 3146 | 2.76261 |
| 2.3 | 37.577 | 3141 | 2.39168 |
| 2.2 | 10.745 | 3056 | 8.22682 |
| 2.0 | 37.223 | 2722 | 2.41360 |
| 2.0 | 17.153 | 2751 | 5.16522 |
| 1.9 | 42.751 | 2620 | 2.11344 |
| 1.9 | 49.339 | 2632 | 1.84556 |
| 1.9 | 17.578 | 2601 | 5.04147 |
| 1.9 | 44.017 | 2595 | 2.05554 |
| 1.8 | 35.493 | 2434 | 2.52721 |
| 1.8 | 12.212 | 2400 | 7.24197 |
| 1.8 | 51.088 | 2486 | 1.78639 |
| 1.8 | 14.231 | 2484 | 6.21876 |
| 1.8 | 11.473 | 2452 | 7.70638 |
| 1.7 | 34.800 | 2254 | 2.57590 |
| 1.7 | 27.837 | 2309 | 3.20237 |
| 1.7 | 53.168 | 2321 | 1.72129 |
| 1.7 | 32.076 | 2364 | 2.78818 |
| 1.6 | 42.017 | 2232 | 2.14866 |
| 1.6 | 23.344 | 2149 | 3.80762 |
| 1.6 | 48.110 | 2165 | 1.88980 |
| 1.6 | 44.924 | 2173 | 2.01611 |
| 1.5 | 29.657 | 1997 | 3.00981 |
| 1.5 | 52.126 | 2030 | 1.75322 |
| 1.5 | 51.429 | 1976 | 1.77534 |
| 1.4 | 49.824 | 1863 | 1.82872 |
| 1.4 | 22.855 | 1899 | 3.88791 |
| 1.3 | 39.143 | 1821 | 2.29951 |
| 1.3 | 20.024 | 1781 | 4.43073 |
| 1.2 | 39.617 | 1655 | 2.27307 |
| 1.2 | 44.627 | 1616 | 2.02884 |
| 1.2 | 48.933 | 1632 | 1.85990 |
| 1.2 | 46.065 | 1676 | 1.96882 |
| 1.1 | 54.567 | 1496 | 1.68044 |
| 1.1 | 53.676 | 1478 | 1.70620 |
| 0.9 | 50.485 | 1194 | 1.80632 |

TABLE C

| Intensity % % | Angle 2-Theta ° | Intensity Count | d value Angstrom |
|---|---|---|---|
| 100.0 | 11.497 | 51807 | 7.69078 |
| 92.8 | 18.989 | 48051 | 4.66972 |
| 91.9 | 18.373 | 47601 | 4.82506 |
| 57.8 | 29.661 | 29967 | 3.00944 |
| 52.6 | 26.195 | 27260 | 3.39929 |

TABLE C-continued

| Intensity % | Angle 2-Theta ° | Intensity Count | d value Angstrom |
|---|---|---|---|
| 43.9 | 17.617 | 22761 | 5.03016 |
| 41.3 | 17.416 | 21402 | 5.08800 |
| 39.2 | 26.600 | 20320 | 3.34840 |
| 26.9 | 23.054 | 13921 | 3.85474 |
| 20.8 | 21.315 | 10787 | 4.16519 |
| 18.5 | 27.656 | 9603 | 3.22288 |
| 18.0 | 35.058 | 9305 | 2.55752 |
| 16.6 | 25.037 | 8587 | 3.55375 |
| 15.5 | 30.658 | 8020 | 2.91384 |
| 14.7 | 9.144 | 7591 | 9.66314 |
| 14.3 | 47.342 | 7386 | 1.91864 |
| 13.5 | 15.694 | 7016 | 5.64216 |
| 13.3 | 39.177 | 6894 | 2.29760 |
| 13.1 | 40.815 | 6798 | 2.20911 |
| 12.8 | 33.025 | 6632 | 2.71021 |
| 11.7 | 30.219 | 6047 | 2.95516 |
| 11.2 | 22.615 | 5815 | 3.92855 |
| 10.7 | 25.478 | 5548 | 3.49328 |
| 10.6 | 37.656 | 5501 | 2.38681 |
| 9.8 | 32.502 | 5102 | 2.75260 |
| 9.3 | 43.613 | 4841 | 2.07363 |
| 9.0 | 21.932 | 4642 | 4.04943 |
| 7.6 | 33.447 | 3920 | 2.67692 |
| 7.5 | 50.824 | 3861 | 1.79505 |
| 7.3 | 31.744 | 3757 | 2.81657 |
| 7.2 | 38.539 | 3712 | 2.33414 |
| 7.1 | 8.766 | 3704 | 10.07914 |
| 6.4 | 38.151 | 3325 | 2.35699 |
| 5.9 | 39.614 | 3059 | 2.27325 |
| 5.7 | 40.003 | 2928 | 2.25202 |
| 5.5 | 28.708 | 2844 | 3.10714 |
| 5.5 | 42.252 | 2838 | 2.13725 |
| 5.2 | 46.505 | 2684 | 1.95118 |
| 5.1 | 32.179 | 2622 | 2.77947 |
| 5.1 | 49.137 | 2653 | 1.85265 |
| 4.9 | 41.496 | 2532 | 2.17442 |
| 4.8 | 35.720 | 2462 | 2.51166 |
| 4.7 | 53.904 | 2424 | 1.69952 |
| 4.6 | 50.322 | 2387 | 1.81176 |
| 4.6 | 44.375 | 2390 | 2.03977 |
| 4.5 | 45.630 | 2357 | 1.98655 |
| 4.4 | 34.018 | 2274 | 2.63334 |
| 4.4 | 48.434 | 2269 | 1.87789 |
| 4.3 | 13.800 | 2245 | 6.41178 |
| 4.1 | 48.905 | 2115 | 1.86089 |
| 3.7 | 47.725 | 1910 | 1.90413 |
| 3.7 | 52.130 | 1941 | 1.75312 |
| 3.5 | 44.816 | 1831 | 2.02071 |
| 3.4 | 34.363 | 1778 | 2.60763 |
| 3.3 | 49.726 | 1685 | 1.83207 |
| 2.9 | 51.819 | 1480 | 1.76290 |
| 2.4 | 52.826 | 1223 | 1.73165 |

TABLE D

| Intensity % | Angle 2-Theta ° | Intensity Count | d value Angstrom |
|---|---|---|---|
| 100.0 | 5.538 | 41111 | 15.94646 |
| 46.1 | 18.281 | 18934 | 4.84898 |
| 41.8 | 14.181 | 17191 | 6.24029 |
| 36.7 | 26.902 | 15108 | 3.31147 |
| 31.5 | 21.115 | 12962 | 4.20427 |
| 30.1 | 15.227 | 12380 | 5.81385 |
| 26.9 | 19.913 | 11041 | 4.45517 |
| 25.3 | 27.485 | 10419 | 3.24253 |
| 24.7 | 21.297 | 10153 | 4.16866 |
| 23.9 | 21.997 | 9837 | 4.03753 |
| 22.8 | 7.589 | 9380 | 11.63992 |
| 20.2 | 22.309 | 8311 | 3.98182 |
| 19.4 | 20.490 | 7969 | 4.33096 |
| 17.4 | 19.192 | 7157 | 4.62084 |
| 17.3 | 16.837 | 7099 | 5.26138 |
| 16.8 | 21.789 | 6910 | 4.07564 |
| 14.6 | 33.813 | 6000 | 2.64879 |
| 14.2 | 11.113 | 5835 | 7.95517 |

TABLE D-continued

| Intensity % | Angle 2-Theta ° | Intensity Count | d value Angstrom |
|---|---|---|---|
| 14.1 | 14.533 | 5788 | 6.08996 |
| 14.0 | 13.216 | 5767 | 6.69382 |
| 13.1 | 18.827 | 5386 | 4.70975 |
| 13.1 | 23.247 | 5377 | 3.82328 |
| 12.4 | 13.764 | 5093 | 6.42847 |
| 12.3 | 25.246 | 5062 | 3.52478 |
| 12.2 | 38.672 | 5024 | 2.32643 |
| 12.1 | 26.074 | 4993 | 3.41479 |
| 12.0 | 32.614 | 4918 | 2.74341 |
| 11.9 | 26.385 | 4903 | 3.37525 |
| 10.9 | 28.010 | 4487 | 3.18301 |
| 10.8 | 22.959 | 4448 | 3.87056 |
| 10.5 | 24.754 | 4315 | 3.59372 |
| 9.8 | 25.723 | 4047 | 3.46059 |
| 9.2 | 31.238 | 3766 | 2.86100 |
| 8.9 | 6.588 | 3670 | 13.40638 |
| 8.9 | 17.236 | 3658 | 5.14068 |
| 8.9 | 33.497 | 3671 | 2.67303 |
| 8.8 | 23.650 | 3608 | 3.75890 |
| 8.5 | 28.589 | 3503 | 3.11977 |
| 8.4 | 9.548 | 3454 | 9.25585 |
| 8.3 | 32.199 | 3429 | 2.77782 |
| 8.2 | 35.988 | 3365 | 2.49355 |
| 7.8 | 31.745 | 3198 | 2.81649 |
| 7.7 | 30.629 | 3185 | 2.91654 |
| 7.2 | 43.549 | 2959 | 2.07654 |
| 6.4 | 40.247 | 2635 | 2.23894 |
| 6.3 | 29.513 | 2577 | 3.02423 |
| 6.2 | 11.850 | 2542 | 7.46215 |
| 6.2 | 11.525 | 2557 | 7.67191 |
| 6.0 | 39.362 | 2459 | 2.28725 |
| 5.8 | 29.763 | 2388 | 2.99932 |
| 5.7 | 37.209 | 2347 | 2.41447 |
| 5.7 | 35.084 | 2341 | 2.55566 |
| 5.6 | 34.920 | 2288 | 2.56735 |
| 5.4 | 42.920 | 2230 | 2.10550 |
| 5.3 | 50.277 | 2171 | 1.81328 |
| 5.2 | 42.171 | 2141 | 2.14112 |
| 5.1 | 44.399 | 2104 | 2.03874 |
| 5.1 | 47.087 | 2105 | 1.92843 |
| 4.8 | 44.883 | 1984 | 2.01788 |
| 4.8 | 41.043 | 1964 | 2.19737 |
| 4.8 | 48.524 | 1977 | 1.87461 |
| 4.7 | 41.756 | 1949 | 2.16144 |
| 4.6 | 52.217 | 1896 | 1.75038 |
| 4.5 | 47.653 | 1833 | 1.90683 |
| 4.4 | 45.491 | 1797 | 1.99231 |
| 4.3 | 46.606 | 1753 | 1.94718 |
| 4.1 | 51.790 | 1686 | 1.76381 |
| 4.1 | 52.977 | 1670 | 1.72707 |
| 3.8 | 53.765 | 1544 | 1.70360 |
| 3.8 | 49.860 | 1566 | 1.82749 |
| 3.7 | 54.616 | 1505 | 1.67904 |
| 3.7 | 50.785 | 1540 | 1.79632 |

TABLE E

| Intensity % | Angle 2-Theta ° | Intensity Count | d value Angstrom |
|---|---|---|---|
| 100.0 | 11.509 | 80550 | 7.68288 |
| 88.9 | 18.375 | 71577 | 4.82446 |
| 47.7 | 18.996 | 38395 | 4.66801 |
| 39.4 | 29.663 | 31775 | 3.00924 |
| 37.6 | 17.621 | 30300 | 5.02903 |
| 31.6 | 26.557 | 25471 | 3.35375 |
| 23.1 | 26.227 | 18586 | 3.39513 |
| 19.9 | 17.420 | 16012 | 5.08659 |
| 17.4 | 35.061 | 14019 | 2.55734 |
| 15.6 | 23.102 | 12552 | 3.84693 |
| 15.5 | 21.313 | 12449 | 4.16563 |
| 13.6 | 47.356 | 10980 | 1.91810 |
| 11.0 | 9.177 | 8839 | 9.62932 |
| 10.3 | 30.668 | 8263 | 2.91285 |
| 9.8 | 27.656 | 7856 | 3.22295 |

TABLE E-continued

| Intensity % % | Angle 2-Theta ° | Intensity Count | d value Angstrom |
|---|---|---|---|
| 9.1 | 25.062 | 7324 | 3.55037 |
| 9.0 | 30.229 | 7221 | 2.95422 |
| 8.4 | 40.824 | 6801 | 2.20864 |
| 8.3 | 39.198 | 6713 | 2.29644 |
| 8.2 | 33.031 | 6574 | 2.70969 |
| 7.1 | 32.540 | 5739 | 2.74944 |
| 7.0 | 43.619 | 5667 | 2.07334 |
| 6.8 | 37.675 | 5479 | 2.38569 |
| 6.4 | 15.725 | 5181 | 5.63083 |
| 6.0 | 22.625 | 4816 | 3.92696 |
| 5.9 | 50.830 | 4723 | 1.79485 |
| 5.8 | 25.490 | 4651 | 3.49160 |
| 5.1 | 21.952 | 4101 | 4.04565 |
| 4.8 | 8.775 | 3836 | 10.06889 |
| 4.7 | 38.545 | 3755 | 2.33381 |
| 4.5 | 5.527 | 3594 | 15.97568 |
| 4.5 | 33.471 | 3606 | 2.67508 |
| 3.9 | 38.157 | 3180 | 2.35664 |
| 3.9 | 39.611 | 3108 | 2.27342 |
| 3.8 | 31.760 | 3099 | 2.81518 |
| 3.4 | 40.021 | 2777 | 2.25107 |
| 3.3 | 49.153 | 2677 | 1.85210 |
| 3.2 | 35.728 | 2583 | 2.51109 |
| 3.2 | 42.280 | 2562 | 2.13589 |
| 3.0 | 50.348 | 2397 | 1.81091 |
| 3.0 | 53.901 | 2391 | 1.69961 |
| 3.0 | 45.624 | 2422 | 1.98681 |
| 3.0 | 28.727 | 2402 | 3.10510 |
| 2.9 | 46.530 | 2297 | 1.95020 |
| 2.8 | 44.398 | 2277 | 2.03878 |
| 2.7 | 13.814 | 2160 | 6.40525 |
| 2.7 | 48.945 | 2162 | 1.85948 |
| 2.7 | 41.498 | 2170 | 2.17432 |
| 2.6 | 10.362 | 2113 | 8.53052 |
| 2.5 | 52.150 | 2030 | 1.75249 |
| 2.5 | 15.984 | 2003 | 5.54035 |
| 2.4 | 48.440 | 1952 | 1.87768 |
| 2.4 | 34.048 | 1959 | 2.63106 |
| 2.3 | 14.199 | 1851 | 6.23275 |
| 2.3 | 13.299 | 1889 | 6.65238 |
| 2.2 | 19.841 | 1764 | 4.47120 |
| 2.1 | 49.823 | 1705 | 1.82874 |
| 2.1 | 44.825 | 1721 | 2.02033 |
| 2.1 | 16.568 | 1697 | 5.34620 |
| 2.0 | 34.364 | 1597 | 2.60758 |
| 1.8 | 51.759 | 1440 | 1.76481 |
| 1.5 | 52.815 | 1215 | 1.73198 |

TABLE F

| Intensity % % | Angle 2-Theta ° | Intensity Count | d value Angstrom |
|---|---|---|---|
| 100.0 | 17.617 | 83975 | 5.03032 |
| 77.1 | 29.686 | 64724 | 3.00698 |
| 68.3 | 19.017 | 57367 | 4.66300 |
| 45.8 | 21.309 | 38434 | 4.16638 |
| 45.5 | 18.355 | 38226 | 4.82971 |
| 27.5 | 26.529 | 23116 | 3.35722 |
| 26.8 | 26.247 | 22523 | 3.39266 |
| 25.7 | 11.491 | 21599 | 7.69436 |
| 18.9 | 25.074 | 15852 | 3.54869 |
| 9.5 | 23.058 | 7987 | 3.85413 |
| 9.2 | 30.672 | 7713 | 2.91250 |
| 8.8 | 15.712 | 7380 | 5.63553 |
| 8.4 | 9.137 | 7017 | 9.67130 |
| 8.0 | 27.742 | 6703 | 3.21314 |
| 7.8 | 21.956 | 6529 | 4.04504 |
| 7.7 | 8.759 | 6452 | 10.08799 |
| 7.4 | 25.505 | 6240 | 3.48957 |
| 5.7 | 22.608 | 4780 | 3.92982 |
| 4.6 | 31.785 | 3850 | 2.81301 |
| 4.0 | 30.194 | 3351 | 2.95753 |
| 3.3 | 8.012 | 2751 | 11.02554 |
| 3.3 | 13.784 | 2760 | 6.41945 |
| 3.2 | 28.753 | 2663 | 3.10240 |
| 2.6 | 15.984 | 2165 | 5.54035 |
| 2.1 | 20.667 | 1741 | 4.29422 |

What is claimed is:

1. A method of treating cytomegalovirus infections, comprising administering to a patient in need of treatment a therapeutically effective amount of a pharmaceutical formulation comprising at least one form of cidofovir, wherein the form of cidofovir is selected from the group consisting of:
   a) cidofovir Form I, characterized by an XRPD pattern having main peaks expressed as 2-theta at about 15.8, 13.5, 24.9, 21.3, 27.0, 18.6, 25.2 and 23.8 degrees;
   b) cidofovir Form II, characterized by an XRPD pattern having main peaks expressed as 2-theta at about 11.5, 19.0, 18.4, 29.7, 26.2, 17.6, 17.4, 26.6, 23.1 and 21.3 degrees;
   c) cidofovir Form III, characterized by an XRPD pattern having main peaks expressed as 2-theta at about 5.5, 18.3, 14.2, 26.9, 21.1, 15.2, 19.9, 27.5, 21.3, 22.0, 7.6 and 22.3 degrees;
   d) cidofovir Form IV, characterized by an XRPD pattern having main peaks expressed as 2-theta at about 11.5, 18.4, 19.0, 29.7, 17.6, 26.6, 26.2 and 17.4 degrees; and
   e) cidofovir Form V, characterized by an XRPD pattern having main peaks expressed as 2-theta at about 17.6, 29.7, 19.0, 21.3, 18.4, 26.5, 26.2 and 11.5 degrees.

2. The method of claim 1, wherein the patient has acquired immune deficiency syndrome.

3. The method of claim 1, wherein the patient has human immunodeficiency virus infection.

* * * * *